United States Patent [19]

Brown

[11] Patent Number: 4,567,176

[45] Date of Patent: Jan. 28, 1986

[54] 4H-IMIDAZOL-4-ONES AND THEIR PHARMACEUTICAL USE

[75] Inventor: Thomas H. Brown, Tewin, England

[73] Assignee: Smith Kline & French Laboratories Limited, Welwyn Garden City, England

[21] Appl. No.: 601,527

[22] Filed: Apr. 18, 1984

[30] Foreign Application Priority Data

Apr. 27, 1983 [GB] United Kingdom ................ 8311443

[51] Int. Cl.$^4$ ..................... A61K 31/55; C07D 401/12
[52] U.S. Cl. .................................... 514/212; 514/317; 514/326; 514/336; 514/389; 546/193; 546/194; 546/210; 546/278; 548/309; 548/311; 548/312; 260/245.5
[58] Field of Search ............... 546/193, 194, 210, 278; 548/309, 311, 312; 514/183, 212, 317, 326, 336, 389; 260/245.5

[56] References Cited

U.S. PATENT DOCUMENTS

| 3,932,644 | 1/1976 | Durant et al. | 546/278 |
|---|---|---|---|
| 3,968,216 | 7/1976 | Black et al. | 546/278 |
| 4,234,588 | 11/1980 | Brown et al. | 544/321 |
| 4,385,058 | 5/1983 | Cooper et al. | 544/321 |

FOREIGN PATENT DOCUMENTS

| 102026 | 3/1984 | European Pat. Off. | 548/309 |
|---|---|---|---|
| 2030979 | 4/1980 | United Kingdom | 544/321 |

OTHER PUBLICATIONS

*Derwent Abstract* 72003C (EP 16,565).

*Primary Examiner*—Robert T. Bond
*Attorney, Agent, or Firm*—Joan S. Keps; Richard D. Foggio; Alan D. Lourie

[57] ABSTRACT

This invention relates to Mannich-furyl(thienyl, pyridyl or phenyl) alkylaminoimidazolinones which have histamine $H_2$-antagonist activity. A specific compound of this invention is 2-[2-(5-dimethylaminomethylfuran-2-ylmethylthio)-ethylamino]-1-methyl-imidazolin-4-one.

24 Claims, No Drawings

4H-IMIDAZOL-4-ONES AND THEIR PHARMACEUTICAL USE

This invention relates to imidazolinone derivatives, and in particular to such derivatives comprising a Mannich group. This invention further relates to processes for their preparation, pharmaceutical compositions containing them and their use as histamine H$_2$-antagonists.

Histamine, a physiologically active compound endogenous in mammals, exerts its action by interacting with certain sites called receptors. One type of receptor is known as a histamine H$_1$-receptor (Ash and Schild, Brit. J. Pharmac. Chemother. 27 427 (1966)) and the actions of histamine mediated through these receptors are blocked by drugs commonly called "antihistamines" (histamine H$_1$-antagonists) a common example of which is mepyramine. A second type of histamine receptor is known as the H$_2$-receptor (Black et al. Nature 1972, 236, 385). These receptors are not blocked by mepyramine but are blocked by burimamide. Compounds which block these histamine H$_2$-receptors are called histamine H$_2$-antagonists.

Histamine H$_2$-antagonists are useful in treating disease conditions caused by the biological effects of histamine mediated through H$_2$-receptors, for example, as inhibitors of gastric acid secretion, in the treatment of inflammation mediated through histamine H$_2$-receptors and as agents which act on the cardiovascular system, for example, as inhibitors of effects of histamine on blood pressure mediated through histamine H$_2$-receptors.

Cimetidine is an example of a histamine H$_2$-antagonist. Cimetidine has been shown to be useful in the treatment of duodenal, gastric, recurrent and stomal ulceration, and reflux oesophagitis and in the management of patients who are at high risk from hemorrhage of the upper gastrointestinal tract.

In some physiological conditions the biological actions of histamine are mediated through both histamine H$_1$- and H$_2$-receptors and blockade of both types of receptors is useful. These conditions include inflammation mediated by histamine, for example skin inflammation, and those hypersensitivity reponses due to the action of histamine at H$_1$- and H$_2$-receptors, for example allergies.

Accordingly the present invention provides a compound of the formula (I):

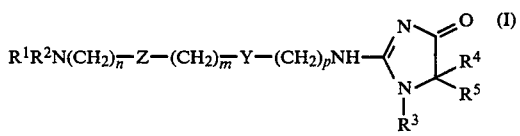

or a pharmaceutically acceptable salt thereof, wherein:

R$^1$ and R$^2$ are independently hydrogen, C$_{1-6}$alkyl, phenyl(C$_{1-6}$)alkyl, furanyl(C$_{1-6}$)alkyl, thienyl(C$_{1-6}$)alkyl, C$_{3-10}$cycloalkyl, hydroxy(C$_{2-6}$)alkyl or halo(C$_{2-6}$)alkyl (wherein said hydroxy and halo groups are not substituted on the carbon atom adjacent to the nitrogen atom); or R$^1$ and R$^2$ together represent —(CH$_2$)$_q$— wherein q is 4 to 7 to form together with the nitrogen atom to which they are attached a 5–8 membered saturated ring;

n is an integer from 1 to 6;

Z is 2,5-furanyl, 2,5-thienyl, 2,4-pyridyl wherein the R$^1$R$^2$N(CH$_2$)$_n$ group is in the 4-position, or 1,3- or 1,4-phenylene;

m is one; or if Z is pyridyl or phenylene m may also be zero;

Y is oxygen, sulphur or methylene;

p is two, three or four;

R$^3$ is hydrogen, or C$_{1-6}$alkyl optionally substituted by phenyl, hydroxy or C$_{1-6}$alkoxy (wherein said hydroxy and C$_{1-6}$alkoxy groups are not substituted on the carbon atom adjacent to the ring nitrogen atom); and R$^4$ and R$^5$ are independently hydrogen, C$_{1-6}$alkyl optionally substituted by phenyl, or phenyl.

When used herein alkyl means groups that are either straight-chained or branched. In general preferred alkyl groups are methyl and ethyl.

Suitably R$^1$ is phenyl(C$_{1-6}$)alkyl for example benzyl or phenethyl, furanylmethyl or thienylmethyl, halo(C$_{2-6}$) alkyl for example 2,2,2-trifluoroethyl, or C$_{3-10}$cycloalkyl for example cyclohexyl. More suitably R$^1$ is C$_{1-6}$alkyl, for example methyl, ethyl or propyl.

Suitably R$^2$ is hydrogen or C$_{1-6}$alkyl, for example methyl, ethyl or propyl.

Suitably R$^1$ and R$^2$ have the same value, for example they both are methyl or they are both ethyl. In another suitable aspect R$^1$ and R$^2$ together with the nitrogen atom to which they are attached form a pyrrolidino, piperidino ring or hexahydroazepino ring, preferably a pyrrolidino or piperidino ring.

Preferably n is one.

Suitably Z is 2,5-furanyl or 2,5-thienyl. In such compounds preferably Y is sulphur. For example R$^1$R$^2$N(CH$_2$)$_n$—Z—(CH$_2$)$_m$—Y— may represent 5-dimethylaminomethylfuran-2-ylmethylthio, 5-piperidinomethylfuran-2-ylmethylthio or 5-pyrrolidinomethylfuran-2-ylmethylthio.

In a preferred aspect Z is 2,4-pyridyl. In an alternative preferred aspect Z is 1,3-phenylene. In each type of compound suitably —(CH$_2$)$_m$Y— is —CH$_2$S— and preferably —(CH$_2$)$_m$Y— is —OCH$_2$—. For example R$^1$R$^2$N(CH$_2$)$_n$—Z—(CH$_2$)$_m$—Y— may represent 4-dimethylaminomethylpyrid-2-ylmethylthio, 4-piperidinomethylpyrid-2-ylmethylthio, 4-dimethylaminomethylpyrid-2-yloxymethyl, 4-piperidinomethylpyrid-2-yloxymethyl, 3-dimethylaminomethylphenoxymethyl, 3-piperidinomethylphenoxymethyl, 3-dimethylaminomethylphenylmethylthio, 3-piperidinomethylphenylmethylthio or 3-hexahydroazepinomethylphenoxymethyl.

Preferably p is 3 when m is zero. Preferably p is 2 when m is one.

Suitably R$^3$ is benzyl or C$_{1-6}$alkyl for example methyl or ethyl in particular methyl. Preferably R$^3$ is hydrogen.

Suitably R$^4$ is hydrogen or C$_{1-6}$alkyl for example methyl or ethyl or is benzyl.

Suitably R$^5$ is hydrogen or C$_{1-6}$alkyl for example methyl or ethyl. In one aspect it is preferred that one of R$^4$ and R$^5$ is hydrogen and the other is hydrogen, benzyl or C$_{1-6}$alkyl for example methyl. In a preferable aspect R$^4$ and R$^5$ have the same value and are both hydrogen or are both C$_{1-6}$alkyl for example methyl. Preferably R$^4$ and R$^5$ are both hydrogen.

The compounds of the formula (I) may exist in equilibrium with following tautomeric forms:

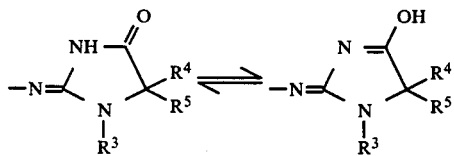

and when $R^3$ is hydrogen:

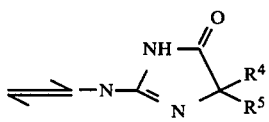

The activity of the pharmaceutically acceptable compounds of formula (I) as histamine $H_2$-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. These are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

The measurement of inhibition of histamine-stimulated secretion of gastric acid from the lumen-perfused stomachs of rats anaesthetised with urethane, and the measurement of inhibition of histamine-induced tachycardia in the isolated guinea pig right atrium, are detailed in European Patent Application Publication No. 0049173.

To illustrate the level of activity of the pharmaceutically acceptable compounds of the invention we have determined that the products of the Examples 1–13 have $ED_{50}$ values in the lumen-perfused rat test of lesss than one micromol $kg^{-1}$ i.v. and $pA_2$ values in the guinea pig atrium test of more than five. In particular most of the compounds of the Examples have $ED_{50}$ values of less than 0.1 micromol $kg^{-1}$ i.v. and $pA_2$ values of more than seven.

In order to use the compounds of the formula (I) or pharmaceutically acceptable salts thereof for medical purposes, they are normally formulated in accordance with standard pharmaceutical practice as pharmaceutical compositions.

The invention further provides pharmaceutical compositions comprising a compound of the formula (I) above or a pharmaceutically acceptable salt thereof and a pharmaceutically acceptable carrier.

The compounds of the formula (I) and their pharmaceutically acceptable salts may be administered orally, parenterally, cutaneously or rectally.

The compounds of the formula (I) and their pharmaceutically acceptable salts which are active when given orally can be formulated as syrups, tablets, capsules and lozenges. A syrup formulation will generally consist of a suspension or solution of the compound or pharmaceutically acceptable salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound of the formula (I) or pharmaceutically acceptable salt thereof in a sterile aqueous carrier or parenterally acceptable oil.

Typical compositions for administration to the skin include lotions and creams in which the compound of the formula (I) or pharmaceutically acceptable salt thereof is contained in a liquid vehicle.

A typical suppository formulation comprises a compound of the formula (I) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains preferably from 0.5 to 25 mg) of a compound of formula (I) or a pharmaceutically acceptable salt thereof calculated as the free base.

The invention also provides a method of blocking histamine $H_2$ receptors which comprises administering to an animal an effective amount to block said receptors of a compound of formula (I) or a pharmaceutically acceptable salt thereof.

The pharmaceutically acceptable compounds of the invention will normally be administered to a subject for the treatment of peptic ulcers and other conditions caused or exacerbated by gastric acidity in the same general manner as that employed for known histamine $H_2$-antagonists, due allowance being made in terms of dose levels for the potency of the compound of the present invention relative to known histamine $H_2$-antagonists. The daily dosage regimen for example for an adult patient may be an oral dose of between 15 mg and 1500 mg, preferably between 20 mg and 250 mg, or an intravenous, subcutaneous, or intramuscular dose of between 0.5 mg and 150 mg, preferably between 1 mg and 20 mg, of the compound of formula (I) or a pharmaceutically acceptable salt thereof calculated as the free base, the composition being administered 1 to 6 times per day.

The compounds of the formula (I) and salts thereof may be prepared by a process which comprises:

(a) reacting a compound of the formula (II) with a compound of the formula (III):

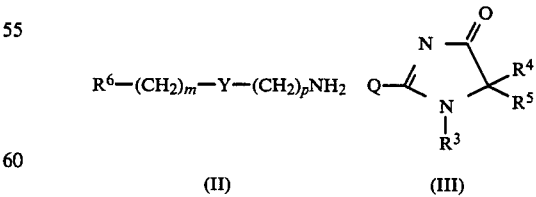

wherein m, Y, p, $R^3$, $R^4$ and $R^5$ are as defined in relation to formula (I), Q is a moiety displaceable by amine, and $R^6$ is a group $R^1R^2N(CH_2)_nZ$- as hereinbefore defined or $R^6$ is a furan-2-yl or thien-2-yl group; or (b) for compounds of the formula (I) wherein m is one and Y is sulphur, reacting a compound of the formula (IV) with a compound of the formula (V) or chemical equivalent thereof:

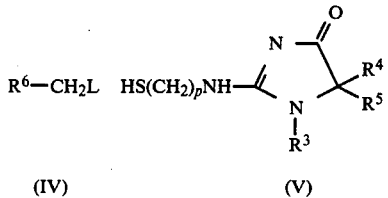

(IV)  (V)

wherein $R^6$, p, $R^3$, $R^4$ and $R^5$ are as defined hereinbefore and L is a moiety displaceable by thiol or chemical equivalent thereof: or (c) for compounds of the formula (I) wherein Z is 2,4-pyridyl, m is zero and Y is oxygen, reacting a compound of the formula (VI) with a compound of the formula (VII) or a derivative thereof that permits reaction to occur:

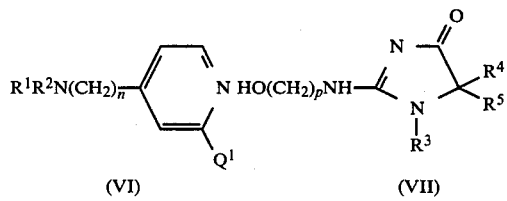

(VI)  (VII)

wherein $R^1$, $R^2$, n, p, $R^3$, $R^4$ and $R^5$ are as hereinbefore defined and $Q^1$ is a group displaceable by hydroxy or the equivalent thereof;

(d) converting a compound of the formula (VIII):

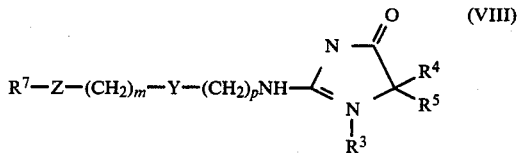

wherein Z, m, Y, p, $R^3$, $R^4$ and $R^5$ are as hereinbefore defined and $R^7$ is a group convertible to a group $R^1R^2N(CH_2)_n$— as hereinbefore defined; or (e) reducing a compound of the formula (IX):

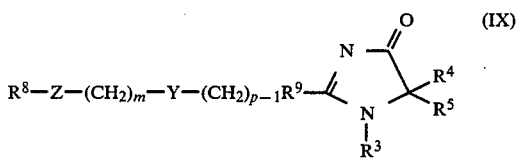

wherein Z, m, Y, p, $R^3$, $R^4$ and $R^5$ are as hereinbefore defined, $R^8$ is a group $R^1R^2N(CH_2)_n$— or a group $R^7$ as hereinbefore defined, and $R^9$ is a group —CONH— or —CH=N—;

(f) for compounds of the formula (I) wherein Z is phenylene, m is zero and Y is oxygen, reacting a compound of the formula (X) or chemical equivalent thereof with a compound of the formula (XI):

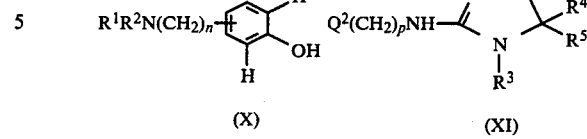

(X)  (XI)

wherein $R^1$, $R^2$, n, p, $R^3$, $R^4$ and $R^5$ are as hereinbefore defined and $Q^2$ is a moiety displaceable by phenol or chemical equivalent thereof; or (g) for compounds of the formula (I) wherein m is one and Y is sulphur, reacting a compound of the formula (XII) or chemical equivalent thereof with a compound of the formula (XIII):

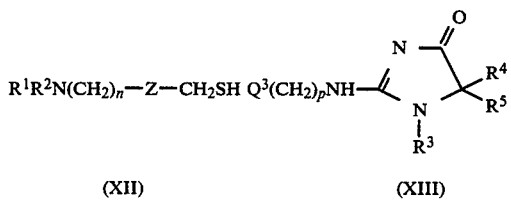

(XII)  (XIII)

wherein $R^1$, $R^2$, n, Z, p, $R^3$, $R^4$ and $R^5$ are as hereinbefore defined and $Q^3$ is a group displaceable by thiol or chemical equivalent thereof;

and thereafter where necessary:

(i) reacting a compound wherein $R^6$ is furan-2-yl or thien-2-yl with a Mannich reagent, to form a compound of the formula (I) wherein n is one, (ii) optionally forming a salt.

In the reaction between the compounds of the formulae (II) and (III) suitable Q is $C_{1-6}$alkylthio, benzylthio, chloro or bromo. Of these methylthio is preferred.

The reaction between a compound of the formula (II) and a compound of formula (III) can be performed in the absence of solvent at an elevated temperature, or in the presence of a substantially inert polar solvent. For example when Q is methylthio the reaction may be carried out in a $C_{1-6}$alkanol, for example ethanol or isopropanol, pyridine or anisole at the reflux temperature of the reaction mixture, or the reaction may be performed in the absence of solvent at elevated temperatures, such as 120°–170° C.

In the reaction between compounds of the formulae (IV) and (V) examples of the moiety L include chloro, bromo, hydroxy, $C_{1-6}$alkoxy for example methoxy, $C_{1-6}$alkanoyloxy for example acetoxy, arylsulphonyloxy for example 4-methylbenzenesulphonyloxy, and $C_{1-6}$alkylsulphonyloxy for example methanesulphonyloxy.

Preferably L is hydroxy in which case the reaction between the compounds of the formulae (IV) and (V) is performed under acidic conditions. When L is chloro or bromo it is preferable to perform the reaction in the presence of a strong base for example sodium ethoxide in ethanol. When L is an arylsulphonyloxy or alkylsulphonyloxy group the reaction is preferably performed under mildly basic conditions for example in pyridine solution.

Suitably in the compounds of the formula (VI), $Q^1$ is chloro or bromo. The reaction of a compound of the formula (VI) with a compound of the formula (VII) is generally performed under basic conditions, for example the anion of the compound of the formula (VII) may be generated, for example using sodium hydride in a suitable solvent. This reaction is particularly suitable for preparing compounds wherein $R^3$ is other than hydrogen.

In the compounds of the formulae (VIII) and (IX) in one suitable aspect $R^7$ is a group $R^1R^2N(CH_2)_xCO(CH_2)_y$— wherein $x+y=n-1$. Favourably x and y are both zero so that the group $R^1R^2NCO$— is a precursor to the group $R_1R^2NCH_2$—. The conversion of such a group $R^1R^2N(CH_2)_x$—$CO(CH_2)_y$— may be performed by reduction for example with a hydride for example lithium aluminium hydride.

In an alternative aspect $R^7$ is a group $CHO$—$(CH_2)_{n-1}$— which may be converted to a group $R^1R^2N(CH_2)_n$— on reaction with an amine $R^1R^2NH$ under conditions of reductive amination. Furthermore in another suitable aspect $R^7$ may be a group $HO(CH_2)_n$— which may be converted directly to $R^1R^2N(CH_2)_n$— or indirectly thereto for example via a moiety such as $Br(CH_2)_n$— and thence to $R^1R^2N(CH_2)_n$—. Such transformations may be carried out in conventional manner.

The compounds of the formula (IX) may be reduced to form compounds of the formula (I), for example using lithium aluminium hydride in an ether solvent when $R^9$ is —CONH—; and for example using a borohydride in an alcohol, lithium aluminium hydride in an ether solvent, or catalytically hydrogenating when $R^9$ is —CH=N—.

In the reaction between the compounds of the formulae (X) and (XI) suitably $Q^2$ is chloro or bromo. Suitably the reaction is performed under basic conditions, for example the anion of the compound of the formula (X) may be generated, for example using sodium hydride. The reaction is performed in a suitable aprotic solvent for example dimethylformamide at a non-extreme temperature for example between 0° C. and 100° C., suitably between ambient and 70° C.

Suitably in the reaction between the compounds of the formulae (XII) and (XIII) $Q^3$ is chloro, bromo, aryl sulphonyloxy for example 4-methylbenzenesulphonyloxy or $C_{1-6}$alkylsulphonyloxy for example methanesulphonyloxy. Such reactions are generally performed in the presence of a base for example triethylamine, an alkoxide or a hydroxide. This reaction is particularly suitable for preparing compounds wherein $R^3$ is other than hydrogen.

For converting a compound wherein $R^6$ is furan-2-yl or thien-2-yl to a compound of the formula (I) wherein n is one suitable Mannich reagents include formaldehyde and an amine $R^1R^2NH$ or salts thereof. Such a reaction may be carried out by treatment of an amine salt with aqueous formaldehyde and a compound wherein $R^6$ is furan-2-yl or thien-2-yl, or by refluxing an amine salt with paraformaldehyde and a compound wherein $R^6$ is furan-2-yl or thien-2-yl, in a convenient solvent such as ethanol. Alternatively where $R^1$ and $R^2$ are both $C_{1-6}$alkyl, the Mannich reagent may be a di-($C_{1-6}$alkyl)methylene ammonium salt for example dimethylmethylene ammonium chloride or iodide, or may be a bis di-$C_{1-6}$alkylaminomethane, for example bis(dimethylamino)methane.

Any group in the remainder of the molecule that is capable of reacting with a Mannich reagent may be optionally protected during the reaction, and may be subsequently deprotected in conventional manner.

The introduction of the group $R^1R^2N(CH_2)_n$— may be performed at any convenient stage of the synthetic procedures outlined herein or in the art. Such introduction may be direct or may involve two or more steps for example converting a hydroxymethyl substituent to bromomethyl and subsequently to $R^1R^2NCH_2$—.

Pharmaceutically acceptable acid addition salts of the compounds of the formula (I) may be prepared from the corresponding base of the compounds of the formula (I) in conventional manner. For example the base may be reacted with an acid in a $C_{1-4}$alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

Suitable pharmaceutically acceptable acid addition salts of the compounds of the formula (I) include those formed with hydrochloride, hydrobromic, sulphuric, phosphoric, acetic, citric, maleic, lactic, ascorbic, fumaric, oxalic, methanesulphonic and ethanesulphonic acids.

The compounds of the formulae (II), (IV) and (XII) may be prepared for example by the methods described in European Patent Application Publication Nos. 3677, 4793, 13071, 15138, 17679, 17680 and 49173 and GB-A-2030979. The compounds of the formula (VI) may be prepared for example by the methods of European Patent Application Publication No. 49173.

The compounds of the formula (III) wherein $R^3$ is hydrogen may for example be prepared by the methods of British Specification No. 1419994. Compounds of the formula (III) wherein $R^3$ is other than hydrogen may for example be prepared by the methods of Rowley, Journal of American Chemical Society, 1971, 93, p 5542-51.

The compounds of the formula (VI) are preparable for example by the methods of European Patent Application Publication No. 49173.

Compounds of the formula (V) may be prepared by the reaction of a corresponding compounds of the formula (III) with an aminoalkylthio wherein the thiol group is optionally protected, if desired. Compounds of the formula (VII) may be prepared by the reaction of the corresponding compounds of the formula (III) with an aminoalkanol. Compounds of the formulae (XI) and (XIII) may be prepared from compounds of the formula (VII) in conventional manner.

The compounds of the formula (VIII) may be prepared in a manner analogous to that described for the preparation of compounds of the formula (I), for example reacting a compound of the formula (III) with an analogue of a compound of the formula (II) wherein $R^6$ is replaced by $R^7$; provided that $R^7$ is suitably protected as necessary.

The compounds of the formula (IX) wherein $R^9$ is CH=N may be prepared by the reaction of a compound of the formula (XIV) with a compound of the formula (XV):

   (XIV)

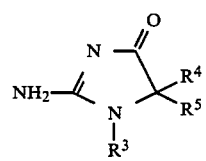   (XV)

wherein $R^8$, Z, m, Y, p, $R^3$, $R^4$ and $R^5$ are as hereinbefore defined, optionally in the presence of an acid catalyst. The compounds of the formula (IX) wherein $R^9$ is —CONH— may be prepared by the reaction of a compound of the formula (X) with an activated derivative of a compound of the formula (XVI):

$$R^8\text{-}Z\text{-}(CH_2)_m\text{-}Y\text{-}(CH_2)_{p-1}CO_2H \qquad (XVI)$$

wherein $R^8$, Z, m, Y and P are as hereinbefore defined. Suitable active derivatives are acyl halides, anhydrides and activated esters. The aldehydes of the formula (XIV) may be prepared for example by reacting a compound of the formula (XVII):

$$R^8\text{-}Z\text{-}OH \qquad (XVII)$$

wherein $R^8$ is as hereinbefore defined, with a protected bromopropionaldehyde (for example protected as a cyclic acetal) and deprotecting. The acid of the formula (XVI) and derivatives thereof may be prepared in similar manner for example by reacting a compound of the formula (XVII) with a protected bromopropionic acid and if necessary deprotecting and/or converting to the desired activated acid derivative.

The following Description and Examples serve to illustrate the invention.

DESCRIPTION 1

1-Ethyl-2-methylthio-imidazolin-4-one hydroiodide (i) 3-Ethyl-4-thiohydantoic acid To a solution of sodium hydroxide (6.0 g) in water (50 ml) was added 1-ethyl-2-thiohydantoin (6.69 g.) The resultant mixture was heated up to 100° C., held at this temperature for 5 minutes and then quickly cooled in an ice-bath. Concentrated hydrochloric acid (20 ml) was added slowly with stirring to the cooled solution. A solid separated out and the mixture was stirred at 0° C. for a further 90 minutes. The solid was collected by filtration, washed with dilute hydrochloric acid and with ethanol.

This solid was purified by slowly adding to dilute aqueous sodium bicarbonate, stirring at 0° C. for 30 minutes, filtering, acidifying the filtrate to pH 1 with concentrated HCl and collecting the solid by filtration (1.44 g), m.p. 196°–198° C.

(ii) 1-Ethyl-2-methylthio-imidazolin-4-one hydroiodide

3-Ethyl-4-thiohydantoic acid (1.44 g) and iodomethane (1.43 g) were refluxed in methanol (15 ml) for 3 hours. The solvent was removed under reduced pressure at 70° C. to give an oily residue which was washed well with diethyl ether to give the title compound as an oily solid (1.50 g).

1-Methyl-2-methylthio-imidazolin-4-one hydroiodide is specifically exemplified by Rowley et al., J.A.C.S. 1971, pages 5542–5551.

EXAMPLE 1

2-[3-(3-Piperidinomethylphenoxy)propylamino]-1-methylimidazolin-4-one 3-(3-Piperidinomethylphenoxy)propylamine (2.61 g), 1-methyl-2-methylthioimidazolin-4-one hydroiodide (2.85 g) and triethylamine (3.635 g) were refluxed in ethanol (25 ml) for 5 hours.

The reaction mixture was cooled, evaporated under reduced pressure and the residue was dissolved in 2N hydrochloric acid (100 ml). This solution was washed with chloroform (2×25 ml), taken to pH 6 with sodium bicarbonate and washed with chloroform (3×30 ml). The aqueous solution was then taken to pH 10 and again washed with chloroform (4×30 ml). The combined chloroform extracts from the pH 6 and pH 10 washings were dried (MgSO$_4$), filtered and evaporated under reduced pressure to give an orange oil which was washed liberally with diethyl ether, to give the title compound as an oil. The oil was crystallised from ethyl acetate/ethanolic HCl and recrystallised firstly from the same solvent system and secondly from isopropanol/methanol to afford 2-[3-(3-piperidinomethylphenoxy)propylamino]-1-methylimidazolin-4-one dihydrochloride, m.p, 257°–259° C.

EXAMPLE 2

2-[2-(5-Dimethylaminomethylfuran-2-ylmethylthio)ethylamino]-1-methyl-imidazolin-4-one 2-(5-Dimethylaminomethylfuran-2-ylmethylthio)ethylamine (2.25 g), 1-methyl-2-methylthio-imidazolin-4-one hydroiodide (2.85 g) and triethylamine (3.635 g) were refluxed in ethanol (25 ml) for 4 hours.

The crude reaction mixture was purified in a similar manner to Example 1 to give the title compound, and was crystallised and recrystallised from ethyl acetate/ethanolic HCl to afford 2-[2-(5-dimethylaminomethylfuran-2-ylmethylthio)ethylamino]-1-methyl-imidazolin-4-one dihydrochloride, m.p. 184°–186° C.

EXAMPLE 3

2-[3-(3-Piperidinomethylphenoxy)propylamino]-imidazolin-4-one 3-(3-Piperidinomethylphenoxy)propylamine (3.01 g), 2-methylthio-imidazolin-4-one hydroiodide (2.60 g) and triethylamine (2.18 g) were refluxed in ethanol (20 ml) for 3 hours.

The reaction mixture was cooled, evaporated under reduced pressure and the residue was dissolved in 2N hydrochloric acid. This solution was extracted twice with chloroform, basified to pH 9.5 with sodium hydroxide solution and the precipitated oil was extracted into chloroform (3 x). These extracts were combined, dried (MgSO$_4$), filtered and evaporated under reduced pressure to give a solid which was washed well with hot diethyl ether. The solid was crystallised and recrystallised from ethyl acetate/methanol to afford the title compound, m.p. 148°–149° C.

EXAMPLE 4

2-[3-(4-Piperidinomethylpyrid-2-yloxy)propyl]-imidazolin-4-one 3-(4-Piperidinomethylpyrid-2-yloxy)propylamine (2.57 g), 2-methylthio-imidazolin-4-one hydroiodide (2.60 g) and triethylamine (2.18 g) were refluxed in ethanol (20 ml) for 5 hours. The mixture was refluxed for a further hour in the presence of additional 2-methylthio-imidazolin-4-one hydroiodide (2.60 g) to ensure completion.

The reaction mixture was cooled, evaporated under reduced pressure, and the residue dissolved in water. The pH of the red solution was taken to 9.5 and it was extracted into chloroform (4 x). These extracts were combined, dried (MgSO$_4$), treated with charcoal, filtered and evaporated under reduced pressure to give an oily solid. This was purified by medium pressure chromatography using chloroform/methanol (17:3) as eluant. The resultant solid was crystallised from isopropanol and recrystallised from isopropanol/methanol to afford the title compound, m.p. 177°–179° C.

EXAMPLE 5

2-[2-(5-Dimethylaminomethylfuran-2-ylmethylthio)ethylamino]-imidazolin-4-one 2-(5-Dimethylaminomethylfuran-2-ylmethylthio)ethylamine (4.00 g), 2-methylthio-imidazolin-4-one hydroiodide (9.63 g) and triethylamine (7.27 g) were refluxed in ethanol (50 ml) for 6 hours.

The reaction mixture as filtered and purified in a manner similar to that of Example 1 to give the title compound. The resultant oily solid was crystallised from isopropanol, dissolved in hot methanol, treated with charcoal, filtered, treated with maleic acid (1.28 g) and evaporated under reduced pressure. The solid residue was recrystallised from isopropanol/methanol and recrystallised from ethanol to afford 2-[2-(5-dimethylaminomethylfuran-2-ylmethylthio)ethylamino]-imidazolin-4-one dimaleate m.p. 126°–127° C.

EXAMPLE 6

2-[3-(4-Piperidinomethylpyrid-2-yloxy)propylamino]-1-methylimidazolin-4-one 3-(4-Piperidinomethylpyrid-2-yloxy)propylamine (3.64 g), 1-methyl-2-methylthio-imidazolin-4-one hydroiodide (7.92 g) and triethylamine (3.635 g) were refluxed in ethanol (40 ml) for 6 hours.

The reaction was cooled and evaporated under reduced pressure to afford an oil. This was dissolved in water and taken to pH 4 with glacial acetic acid, whereupon it was extracted with chloroform (4 x). The aqueous solution was then taken to pH 9.5 with dilute sodium hydroxide, and the precipitated oil extracted into chloroform (5 x). These extracts were combined, dried (MgSO$_4$) and evaporated under reduced pressure to give a red oily solid. This solid was purified using medium pressure chromatography with gradient elution (chloroform→chloroform/methanol (9:1). The desired fractions were collected and evaporated under reduced pressure to afford the title compound as an oil. This was dissolved in methanol containing maleic acid (1.60 g) and evaporated under reduced pressure to give a residue which was crystallised from diethyl ether/ethanol to yield 2-[3-(4-piperidinomethylpyrid-2-yloxy)propylamino]-1-methyl-imidazolin-4-one dimaleate m.p. 118°–120° C.

EXAMPLE 7

2-[3-(3-Piperidinomethylphenoxy)propylamino]-5-benzylimidazolin-4-one 3-(3-Piperidinomethylphenoxy)propylamine (2.50 g) 5-benzyl-2-methylthio-imidazolin-4-one hydroiodide (3.48 g) and triethylamine (2.18 g) were refluxed in ethanol (50 ml) for 6 hours.

The crude reaction mixture was purified in a similar manner to that of Example 3 to afford an oil. This oil was crystallised from isopropanol/ethanol to give the title compound as a white crystalline solid (0.97 g), m.p. 144°–145° C. (recrystallised from isopropanol).

EXAMPLE 8

2-[3-(3-Piperidinomethylphenoxy)propylamino]-5,5-dimethylimidazolin-4-one 3-(3-Piperidinomethylphenoxy)propylamine (2.43 g) 5,5-dimethyl-2-methylthio-imidazolin-4-one hydroiodide (2.80 g) and triethylamine (2.18 g) were refluxed in ethanol (50 ml) for 5 hours.

The crude reaction mixture was purified in a similar manner to that of Example 3 to afford an oil. This oil was crystallised from isopropanol/ethanol to give the title compound as a white crystalline solid (1.08 g), m.p. 152°–153° C.

EXAMPLE 9

2-[3-(3-Piperidinomethylphenoxy)propylamino]-5-methyimidazolin-4-one 3-(3-Piperidinomethylphenoxy)propylamine (2.50 g), 5-methyl-2-methylthio-imidazolin-4-one (2.73 g) and triethylamine (2.05 g) were refluxed in ethanol (30 ml) for 5 hours.

The crude reaction mixture was purified in a similar manner to that of Example 3 to afford an oil, which was converted to an amorphous, hygroscopic solid (1.05 g), m.p. 103°–105° C. using isopropanol/diethyl ether.

Final purification was achieved by dissolving this solid in dilute hydrochloric acid, basifying with 2N sodium hydroxide to pH 9 and extracting with chloroform (3 X). After drying over MgSO$_4$, the chloroform extracts were evaporated under reduced pressure to give a colourless oil which crystallised from isopropanol/diethyl ether to give the title compound as a white, crystalline solid (0.52 g), m.p. 118°–119° C.

EXAMPLE 10

2-[2-(4-Dimethylaminomethyl)pyrid-2-ylmethylthio)ethylamino]-imidazoline-4-one 2-(4-(Dimethylaminomethyl)pyrid-2-ylmethylthio)ethylamine (2.25 g), 2-methylthio-imidazolin-4-one hydroiodide (2.58 g) and triethylamine (2.18 g) were refluxed in ethanol (50 ml) for 6 hours.

The reaction mixture was allowed to cool and evaporated under reduced pressure. The oily residue was dissolved in 2N hydrochloric acid (75 ml) and washed with chloroform (3×25 ml). The acidic layer was taken to pH 10 with 2N sodium hydroxide and extracted with chloroform for 24 hours in a continuous liquid-liquid-extractor. The chloroform extract was dried (MgSO$_4$), and evaporated under reduced pressure to give the title compound as a yellow oil.

This oil was dissolved in ethanol and maleic acid (3 equivalents) in ethanol was added. The solution was evaporated under reduced pressure to give a solid residue which was crystallised from isopropanol/methanol to give 2-[2-(4-dimethylaminomethyl)pyrid-2-ylmethylthio)ethylamino]-imidazoline-4-one trimaleate (3.14 g), m.p. 120.5°–121.5° C. (recrystallisation from ethanol).

EXAMPLE 11

2-[3-(3-Piperidinomethylphenoxy)propylamino]-1-ethylimidazolin-4-one 3-(3-Piperidinomethylphenoxy)propylamine (2.25 g) 1-ethyl-2-methylthio-imidazolin-4-one (4.99 g) and triethylamine (3.635 g) were refluxed in ethanol (50 ml) for 6 hours.

The crude reaction mixture was purified in a manner similar to that of Example 1 to afford an oil. This oil was subjected to column chromatography on silica gel using chloroform:methanol (9:1) as eluant. The desired fractions were collected, combined and evaporated under reduced pressure to give the title compound as an oily residue. This was crystallised from ethanol/ethanolic HCl to afford 2-[3-(3-piperidinomethylphenoxy)-propylamino]-1-ethyl-imidazolin-4-one dihydrochloride (0.73 g) as a pale yellow crystalline solid, m.p. 216°–218° C.

EXAMPLE 12

2-[3-(3-Hexahydroazepinomethylphenoxy)-propylamino]-imidazolin-4-one 3-(3-Hexahydroazepinomethylphenoxy)propylamine (2.62 g), 2-methylthio-imidazolin-4-one hydroiodide (2.58 g) and triethylamine (2.18 g) were refluxed in ethanol (50 ml) for 5 hours.

The crude reaction mixture was purified in a manner similar to that of Example 3 to afford a dark red oil. This was crystallised by trituration under diethyl ether and recrystallised from isopropanol/ethanol to afford the title compound (1.38 g) m.p. 135°–137° C. (recrystallisation from isopropanol/ethanol).

EXAMPLE 13

2-[3-(3-Hexahydroazepinomethylphenoxy)-propylamino]-1-methylimidazolin-4-one 3-(3-Hexahydroazepinomethylphenoxy)propylamine (2.62 g), 1-methyl-2-methylthio-imidazolin-4-one hydroiodide (2.71 g) and triethylamine (2.18 g) were refluxed in ethanol (50 ml) for 6 hours.

The crude reaction mixture was purified in a manner similar to that of Example 3 to afford the title compound as a red oil.

This oil as crystallised from ethanol/ethanolic HCl to give a solid which was recrystallised from ethanol/methanol to afford 2-[3-(3-hexahydroazepinomethylphenoxy)propylamino]-imidazolin-4-one dihydrochloride (1.01 g), m.p. 243°–243.5° C.

This solid (which contained a trace of iodide) was dissolved in water (20 ml), the solution was basified to about pH 10 with 2N sodium hydroxide and extracted with chloroform (5 times). The chloroform extracts were dried and evaporated under reduced pressure to give an oil which was dissolved in ethanol and ethanolic HCl added. Evaporation under reduced pressure gave the dihydrochloride as a white solid which as recrystallised from ethanol (0.91 g), m.p. 241°–242° C.

EXAMPLE 14

2-[2-(4-(Dimethylaminomethyl)pyrid-2-ylmethylthio)ethylamino]-1-methyl-imidazolin-4-one 2-(4-(Dimethylaminomethyl)pyrid-2-ylmethylthio)ethylamine (2.25 g), 1-methyl-2-methylthio-imidazolin-4-one hydroiodide (2.71 g) and triethylamine (2.18 g) were refluxed in ethanol (50 ml) for 6 hours.

The reaction mixture was allowed to cool and evaporated under reduced pressure. The resultant oil was dissolved in 2N hydrochloric acid (100 ml) and washed with chloroform (3×40 ml). The acidic layer was basified to pH 10 with aqueous sodium bicarbonate and extracted with chloroform for 5 hours in a continuous liquid-liquid extractor. The chloroform extract was dried (MgSO$_4$) and evaporated under reduced pressure to give a red oil which was washed thoroughly with diethyl ether to afford the title compound as an oil; mass spectrum 321, 278, 208, 181, 172, 150, 141, 107, 58, 44, 42.

EXAMPLE 15

2-[3-(3-Piperidinomethylphenoxy)propylamino]-1-benzylimidazolin-4-one (i) 1-Benzyl-2-thiohydantoin Ammonium thiocyanate (47.27 g) and N-benzylglycine ethyl ester (40.0 g) were fused together at 140° C. for 4 hours. The deep red solution was allowed to cool to room temperature and the solid residue washed with ethanol/water (1:1) (200 ml). The solid was collected by filtration, washed with ethanol/water (1:1) (5×200 ml) and with diethyl ether (3×100 ml) to afford 1-benzyl-2-thiohydantoin (24.72 g), m.p. 150°–152° C.

(ii) 1-Benzyl-2-methylthio-2-imidazolin-4-one hydroiodide

1-Benzyl-2-thiohydantoin (8.07 g), iodomethane (10 ml) and methanol (50 ml) were warmed at 40°–42° C. for 8 hours. The reaction mixture was evaporated under reduced pressure, the residue was washed with diethyl ether and recrystallised from methanol-ethanol to give 1-benzyl-2-methylthio-2-imidazolin-4-one hydroiodide (4.86 g) m.p. 185°–190° C., as an impure light-buff coloured solid which was taken on to the next stage.

(iii) 2-[3-(3-Piperidinomethylphenoxy)propylamino]-1-benzyl-imidazolin-4-one

1-Benzyl-2-methylthio-2-imidazolin-4-one hydroiodide (2.09 g) from the previous stage, 3-(3-piperidinomethylphenoxy)propylamine (1.49 g) and triethylamine (1.27 g) were refluxed in ethanol (35 ml) for 7 hours with stirring. The solution was allowed to cool overnight and evaporated under reduced pressure to give a residue. This residue was dissolved in 2N hydrochloric acid (30 ml), and extracted with chloroform (3×20 ml). The aqueous layer was taken to pH 10 with 2N sodium hydroxide and extracted with chloroform (3×30 ml). The latter chloroform extracts were dried (MgSO$_4$) and evaporated under reduced pressure. The residue was washed thoroughly with cold diethyl ether and treated with dilute ethanolic HCL. Excess solvent was evaporated and the residue recrystallised from isopropanolacetone to afford 2-[3-(3-piperidinomethylphenoxy)propylamino]-1-benzylimidazolin-4-one dihydrochloride, m.p. 95°–98° C.

EXAMPLE 16

By a method similar to that of Example 1, 2-methylthioimidazolin-4-one is reacted with:
(a) 2-(5-methylaminomethylthien-2-ylmethylthio)ethylamine,
(b) 3-(3-pyrrolidinomethylphenoxy)propylamine,
(c) 3-(4-piperidinomethylphenoxy)propylamine,
(d) 4-(3-piperidinomethylphenyl)butylamine,
(e) 2-(5-benzylaminomethylfuran-2-ylmethylthio)ethylamine,
(f) 2-(5-furan-2-ylmethylaminomethylfuran-2-ylmethylthio)-ethylamine,
(g) 2-(5-thien-2-ylmethylaminomethylfuran-2-methylthio)-ethylamine,
(h) 2-(5-hydroxyethylaminomethylfuran-2-ylmethylthio)ethylamine,
(i) 2-(5-N-(2,2,2-trifluoroethyl)-N-methylaminomethylfuran-2-ylmethylthio)ethylamine,
(j) 2-(5-cyclohexylmethylaminomethylfuran-2-ylmethylthio)ethylamine, or an acid addition salt thereof to yield respectively;
(a) 2-[2-(5-methylaminomethylthien-2-ylmethylthio)ethylamino]-imidazolin-4-one,
(b) 2-[3-(3-pyrrolidinomethylphenoxy)propylamino]imidazolin-4-one,
(c) 2-[3-(4-piperidinomethylphenoxy)propylamino]imidazolin-4-one,
(d) 2-[4-(3-piperidinomethylphenyl)butylamino]-imidazolin-4-one,
(e) 2-[2-(5-benzylaminomethylfuran-2-ylmethylthio)ethylamino]-imidazolin-4-one,
(f) 2-[2-(5-furan-2-ylmethylaminomethylfuran-2-ylmethylthio)-ethylamino]-imidazolin-4-one,
(g) 2-[2-(5-thien-2-ylmethylaminomethylfuran-2-ylmethylthio)-ethylamino]-imidazolin-4-one,
(h) 2-[2-(5-hydroxyethylaminomethylfuran-2-ylmethylthio)ethylamino]-imidazolin-4-one,
(i) 2-[2-(5-(5-N-(2,2,2-trifluoroethyl)-N-methylaminomethylfuran-2-ylmethylthio)ethylamino]-imidazolin-4-one,
(j) 2-[2-(5-cyclohexylmethylaminomethylfuran-2-ylmethylthio)-ethylamino]-imidazolin-4-one
or a pharmaceutically acceptable acid addition salt thereof.

EXAMPLE 17

By a method similar to that of Example 1, 3-(3-piperidinomethylphenoxy)propylamine is reacted with:
(a) 1-(2-hydroxyethyl)-2-methylthio-imidazolin-4-one,
(b) 1-(2-methoxyethyl)-2-methylthio-imidazolin-4-one, or
(c) 5,5-diphenyl-2-methylthio-imidazolin-4-one,
or an acid addition salt thereof, to yield, respectively:
(a) 2-[3-(3-piperidinomethylphenoxy)propylamino]-1-(2-hydroxyethyl)-imidazolin-4-one,
(b) 2-[3-(3-piperidinomethylphenoxy)propylamino]-1-(2-methoxyethyl)-imidazolin-4-one, or
(c) 2-[3-(3-piperidinomethylphenoxy)propylamino]-1-5,5-diphenyl-imidazolin-4-one,
or a pharmaceutically acceptable acid addition salt thereof.

EXAMPLE 18

A pharmaceutical composition for oral administration is prepared containing:

| | | % by weight |
|---|---|---|
| A | 2-[3-(3-piperidinomethylphenoxy)propylamino]-1-methylimidazolin-4-one | 55 |
| | Dibasic calcium phosphate dihydrate | 20 |
| | Approved colouring agent | 0.5 |
| | Polyvinylpyrrolidone | 4.0 |
| B | Microcrystalline Cellulose | 8.0 |
| | Maize Starch | 8.0 |
| | Sodium glycollate | 4.0 |
| | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 100 mg, 150 mg or 200 mg of the free base.

Other compounds of the invention, for example those specifically described in Examples 2 to 15 can be formulated into pharmaceutical compositions by a similar procedure.

The compounds of this invention show no overt signs of toxicity at doses which are a pertinent multiple of the therapeutic dose.

What is claimed is:
1. A compound of the formula (I):

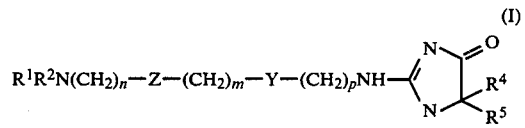

or a pharmaceutically acceptable salt thereof, wherein:
$R^1$ and $R^2$ are independently hydrogen, $C_{1-6}$alkyl, phenyl($C_{1-6}$)alkyl, furanyl($C_{1-6}$)alkyl, thienyl($C_{1-6}$) alkyl, $C_{3-10}$cycloalkyl, hydroxy($C_{2-6}$) alkyl or halo($C_{2-6}$)alkyl (wherein said hydroxy and halo groups are not substituted on the carbon atom adjacent to the nitrogen atom); or
$R^1$ and $R^2$ together represent —$(CH_2)_q$— wherein q is 4 to 7 to form together with the nitrogen atom to which they are attached a 5–8 membered saturated ring;
n is an integer from 1 to 6;
Z is 2,5-furanyl, 2,5-thienyl, 2,4-pyridyl wherein the $R^1R^2N(CH_2)_n$ group is in the 4-position, or 1,3- or 1,4-phenylene;
m is one; or if Z is pyridyl or phenylene m may also be zero;
Y is oxygen, sulphur or methylene;
p is two, three of four;
$R_3$ is hydrogen, or $C_{1-6}$alkyl optionally substituted by phenyl, hydroxy or $C_{1-6}$alkoxy (wherein said hydroxy and $C_{1-6}$alkoxy groups are not substituted on the carbon atom adjacent to the ring nitrogen atom); and
$R^4$ and $R^5$ are independently hydrogen, $C_{1-6}$alkyl optionally substituted by phenyl, or phenyl.
2. A compound according to claim 1 wherein $R^3$ is hydrogen.
3. A compound according to claim 1 wherein $R^3$ is $C_{1-6}$alkyl.
4. A compound according to claim 1 wherein one of $R^4$ and $R^5$ is hydrogen and the other is hydrogen or $C_{1-6}$alkyl.
5. A compound according to claim 1 which is 2-[3-(3-piperidinomethylphenoxy)propylamino]-1-methyl-imidazolin-4-one or a pharmaceutically acceptable salt thereof.
6. A compound according to claim 1 which is 2-[2-(5-dimethylaminomethylfuran-2-ylmethylthio)ethylamino]-1-methylimidazolin-4-one or a pharmaceutically acceptable salt thereof.
7. A compound according to claim 1 which is 2-[3-(3-piperidinomethylphenoxy)propylamino]-imidazolin-4-one or a pharmaceutically acceptable salt thereof.
8. A compound according to claim 1 which is 2-[3-(4-piperidinomethylpyrid-2-yloxy)propyl]-imidazolin-4-one or a pharmaceutically acceptable salt thereof.
9. A compound according to claim 1 which is 2-[2-(5-dimethylaminomethylfuran-2-ylmethylthio)ethylamino]-imidazolin-4-one or a pharmaceutically acceptable salt thereof.
10. A compound according to claim 1 which is 2-[3-(4-piperidinomethylpyrid-2-yloxy)propylamino]-1- methyl-imidazolin-4-one or a pharmaceutically acceptable salt thereof.

11. A compound according to claim 1 which is 2-[3-(3-piperidinomethylphenoxy)propylamino]-5-benzyl-imidazolin-4-one or a pharmaceutically acceptable salt thereof.

12. A compound according to claim 1 which is 2-[3-(3-piperidinomethylphenoxy)propylamino]-5,5-dimethyl-imidazolin-4-one or a pharmaceutically acceptable salt thereof.

13. A compound according to claim 1 which is 2-[3-(3-piperidinomethylphenoxy)propylamino]-5-methyl-imidazolin-4-one or a pharmaceutically acceptable salt thereof.

14. A compound according to claim 1 which is 2-[2-(4-dimethylaminomethyl)pyrid-2-ylmethylthio)ethylamino]-imidazolin-4-one or a pharmaceutically acceptable salt thereof.

15. A compound according to claim 1 which is 2-[3-(3-piperidinomethylphenoxy)propylamino]-1-ethyl-imidazolin-4-one or a pharmaceutically acceptable salt thereof.

16. A compound according to claim 1 which is 2-[3-(3-hexahydroazepinomethylphenoxy)propylamino]-imidazolin-4-one or a pharmaceutically acceptable salt thereof.

17. A compound according to claim 1 which is 2-[3-(3-hexahydroazepinomethylphenoxy)propylaminol-1-methyl-imidazolin-4-one or a pharmaceutically acceptable salt thereof.

18. A compound according to claim 1 which is 2-[2-(4-(dimethylaminomethyl)pyrid-2-ylmethylthio)ethylamino]-1-methyl-imidazolin-4-one or a pharmaceutically acceptable salt thereof.

19. A compound according to claim 1 which is 2-[3-(3-piperidinomethylphenoxy)propylamino]-1-benzyl-imidazolin-4-one.

20. A compound according to claim 1 which is 2-[3-(3-piperidinomethylphenoxy)propylamino]-1-methylimidazolin-4-one dihydrochloride.

21. A compound according to claim 1 which is 2-[3-(3-piperidinomethylphenoxy)propylamino]-imidazolin-4-one.

22. A compound according to claim 1 which is 2-[3-(3-piperidinomethylphenoxy)propylamino]-imidazolin-4-one.

23. A pharmaceutical composition having histamine $H_2$-antagonist activity which comprises a compound according to claim 1 and a pharmaceutically acceptable carrier.

24. A method of blocking histamine $H_2$-receptors which comprises administering to a subject an effective amount to block said receptors of a compound according to claim 1.

* * * * *

UNITED STATES PATENT AND TRADEMARK OFFICE
CERTIFICATE OF CORRECTION

PATENT NO. : 4,567,176
DATED : January 28, 1986
INVENTOR(S) : Thomas H. Brown

It is certified that error appears in the above-identified patent and that said Letters Patent is hereby corrected as shown below:

Column 3, lines 11-15, the structural formula should appear as follows:

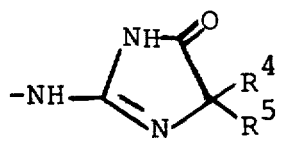

Signed and Sealed this

Twentieth Day of May 1986

[SEAL]

Attest:

DONALD J. QUIGG

Attesting Officer

Commissioner of Patents and Trademarks